United States Patent [19]

Virag

[11] 4,030,495

[45] June 21, 1977

[54] TWIN CHECK VALVE PUMP SYSTEM HAVING FAIL-SAFE CHARACTERISTIC

[75] Inventor: Robert Anthony Virag, Lake Zurich, Ill.

[73] Assignee: Baxter Travenol Laboratories, Inc., Deerfield, Ill.

[22] Filed: Nov. 7, 1975

[21] Appl. No.: 629,835

[52] U.S. Cl. .................. 128/214.2; 128/214 F; 128/273; 137/197; 417/435
[51] Int. Cl.² ........................................ A61M 5/18
[58] Field of Search ....... 128/214 R, 214 C, 214 E, 128/214 F, 214.2, DIG. 12, DIG. 13, 273; 417/435; 137/197; 55/159

[56] References Cited

UNITED STATES PATENTS

| | | | |
|---|---|---|---|
| 3,033,911 | 5/1962 | Duddy | 137/197 X |
| 3,559,644 | 2/1971 | Stoft et al. | 128/214 F |
| 3,572,375 | 3/1971 | Rosenberg | 128/274 X |
| 3,650,093 | 3/1972 | Rosenberg | 128/214.2 X |
| 3,803,810 | 4/1974 | Rosenberg | 55/159 |

Primary Examiner—Dalton L. Truluck
Attorney, Agent, or Firm—Garrettson Ellis; Paul C. Flattery

[57] ABSTRACT

A twin check valve pumping system for use with a syringe or other variable volume pumping device for the pumping of liquids. Along a flow path between the check valves, a porous, hydrophobic member is positioned, in communication with a portion of the flow path upstream of the first, inlet check valve. The second, downstream outlet check valve is biased so that pressure in the conduit between the check valves is required for expulsion of liquid. When gas enters the system, such pressure cannot be achieved, because, upon attempted pressurization of the area between the two check valves, the gas passes through the porous, hydrophobic member back to a position upstream of the first, inlet valve. However, aqueous liquids cannot pass through the porous member, and accordingly the device pumps such liquids normally in the absence of gas.

9 Claims, 4 Drawing Figures

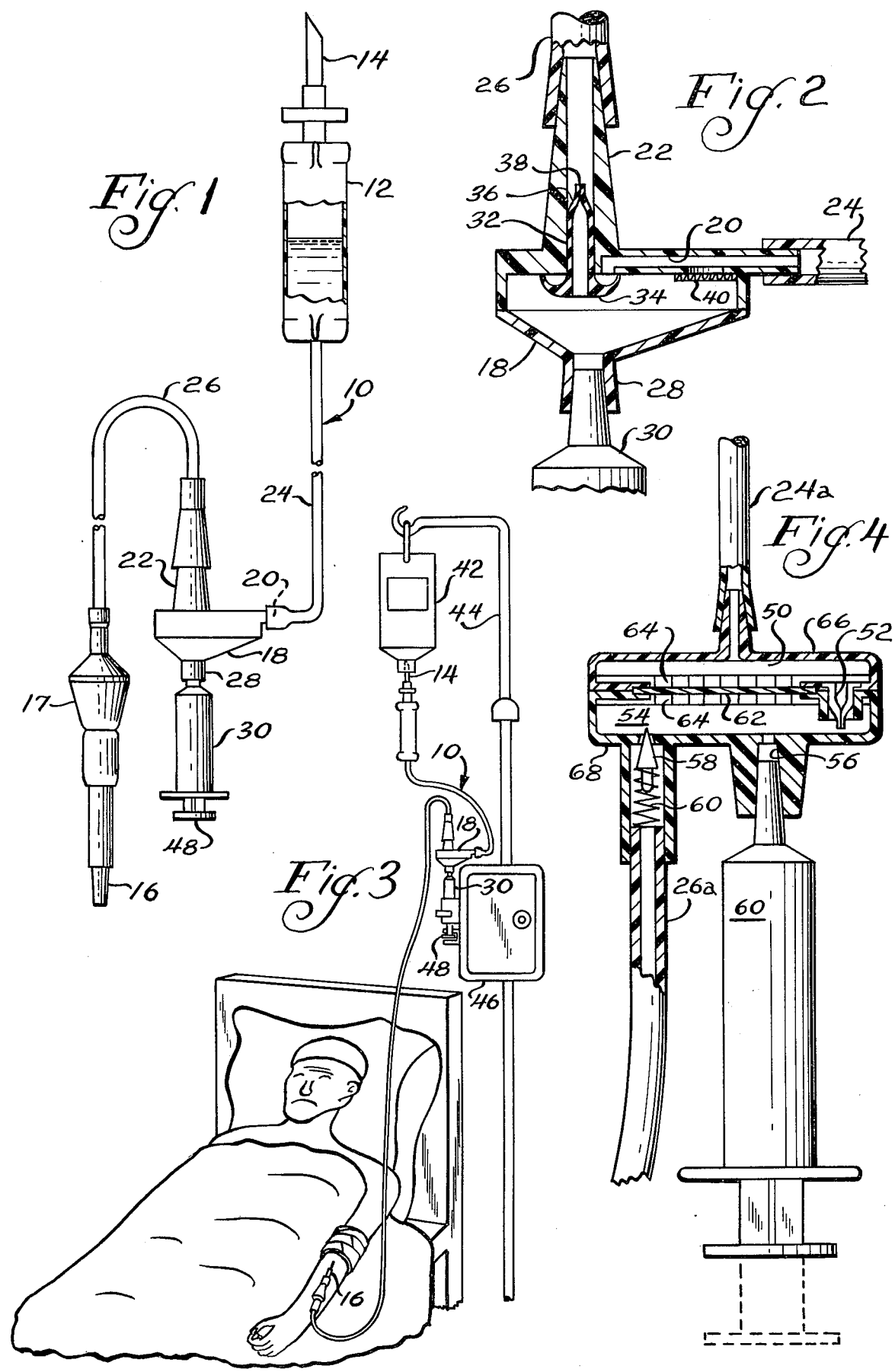

TWIN CHECK VALVE PUMP SYSTEM HAVING FAIL-SAFE CHARACTERISTIC

BACKGROUND OF THE INVENTION

In U.S. Pat. No. 3,447,479, as well as many other sources of technical literature, parenteral solution infusion pumps are disclosed in which a reciprocating syringe or other volume varying device is in communication with a chamber having upstream and downstream one-way valves, each positioned to permit flow only in the downstream direction. When this structure is made part of a parenteral solution administration set, reciprocation of the syringe back and forth at a controlled rate can result in the administration of precisely controlled amounts of parenteral solution to the patient.

A danger of this type of structure exists, in that a pumped syringe administration set will pump air as readily as it will pump liquids, the result of which can be fatal for the patient. As a result of this, "air eliminator" units, for example those described in Rosenberg U.S. Pat. No. 3,523,408, have been proposed to vent air from the set, to prevent its administration to the patient.

These air eliminator units comprise a porous, hydrophobic membrane and a porous, hydrophilic membrane, generally closely spaced together, in which the hydrophobic membrane communicates with the exterior of the administration set, and the hydrophilic membrane functions as a brrier across the flow path of the set.

However, if the hydrophilic membrane barrier is defective, the air eliminator device will be inoperative, and air can be pumped into the patient with potentially fatal results.

A need therefore exists for a fluid-pumping structure, capable of use in an administration set, which prevents the pumping of air, and which is fail-safe, in that any membrane rupture in the device will not result in the pumping of air to the patient.

Also, it is desirable for administration sets to be completely closed from the exterior, so that there can be no contamination through failure of a membrane or the like.

There also is a need for a safe administration set which can pump viscous solutions and solutions containing particulate matter, such as blood, elemental diet solutions, and other solutions having undissolved solids in suspension, such colloids, which might tend to clog the hydrophilic filter of a conventional air eliminator set.

The invention of this application provides a pump device which can be incorporated in a parenteral solution set, a blood administration set, or the like, having the above advantages over the apparatus of the prior art. The pump apparatus structure of this invention can also be used for other purposes in which it may be desired to pump liquid while preventing the pumping of gas.

DESCRIPTION OF THE INVENTION

The invention of this application relates to a twin check pump device which comprises a pumping chamber, a first, one-way inlet valve communicating with said pumping chamber and adapted to permit fluid to flow therein, and a second, one-way outlet valve cummunicating with the pumping chamber and adapted to permit fluid flow out of said chamber. The outlet valve is biased to prevent outflow of fluid below a predetermined pressure. An upstream inlet flow path provides fluid to the pumping chamber through the inlet valve.

In accordance with this invention, a porous member faces the interior of the pumping chamber on one side of the member, and faces the inlet flow path on its other side, to permit selective fluid communication between the pumping chamber and the inlet flow path. The porous member is usually a membrane and is capable of allowing passage of a first material such as a gas, while preventing the passage of a second material such as aqueous liquid. Accordingly, the apparatus is capable of pumping the second material, and is prevented from pumping in the presence of substantial quantities of the first material.

Typically, the pumping chamber is a small, rigid chamber adapted for fluid communication with a syringe member or the like. However, any other expedient for providing a variable volume chamber can be used.

The one-way valves utilized herein may include any desired type of check valve, such as duckbill valves, umbrella valves, spring loaded ball valves, sleeve valves, diaphragm valves, reed valves, and the like.

The porous membrane which defines part of the pumping chamber is typically made of a hydrophobic material such as polytetrafluoroethylene, having a pore size sufficient to permit the flow of gas, while preventing the flow of aqueous liquids such as blood, parenteral solutions, and the like. For example, Celgard$^{TM}$ 2400 Standard Laminate, made by Celanese Corporation, or Fluorpor$^{Tm}$ expanded filters of the Millipore Corporation, are commercially available materials which are highly resistant to the passage of water while readily allowing the passage of air. However, any other porous, hydrophobic material having the desired characteristics of permitting the passage of air while preventing passage of aqueous liquids can be utilized in this invention.

Alternatively, it is contemplated that porous, hydrophilic membrane material such as rayon fabric, can be selected as the porous membrane, so that, when wetted, they will allow the passage of aqueous liquids without permitting the passage of gas. Accordingly, a pump for gas can be made in accordance with this invention, in which the presence of excessive water will cause the pumping action to cease, to prevent the pumping of water.

The structure of this invention is specifically contemplated for use in conjunction with a parenteral administration set. Such a set can be desirably used to precisely pump, by mechanical manipulation of a syringe using a currently known syringe pump, or the like, to provide precisely measured quantities of parenteral solution to a patient.

Such a set can be designed to terminate pumping action when an excessive amount of air enters the pumping chamber, so that air cannot be pumped to the patient. Nevertheless, the set is easy to prime and is fail-safe, since, if the porous member has ruptured, the unit will not pump, and the patient will not be harmed by receiving pumped air.

Furthermore, the structure of this invention can be used to administer colloidal suspensions such as intravenous fat or polypeptide emulsions and blood, as well as viscous solutions, without clogging of any filter barrier, since liquids do not pass through any porous, membranous structures. This eliminates the problem of occluding the pores of hydrophilic membrane structures, which can occur in the prior art air eliminator filters.

Also, the structure of this invention is completely enclosed from the exterior, and does not vent to the outside.

In the drawings,

FIG. 1 is an elevational view of a parenteral solution administration set, utilizing this present invention.

FIG. 2 is a longitudinal sectional view, in enlarged form, of one embodiment of the pumping device of this invention, as used in the set of FIG. 1.

FIG. 3 is a perspective view of the set of FIG. 1 in use, connected to a parenteral solution source, and a syringe pumping apparatus, shown in the process of infusing solution to a patient.

FIG. 4 is an enlarged, elevational view, taken partly in section, of another embodiment of a pumping apparatus of this invention, shown in conjunction with related parts.

Referring to FIGS. 1 through 3, solution administration set 10 is shown to include a conventional drip chamber 12, spike 14, for communication with a parenteral solution container, and an infusion needle hub 16, for receiving an infusion needle or an intravenous catheter as desired. Conventional flashback site 17 is also provided.

As is common to solution administration sets in which the solution is to be pumped to the patient, a pump chamber housing 18 is provided, having an upstream inlet 20 and a downstream outlet 22, both being in communication with lengths of flexible tubing 24, 26. Syringe port 28 is provided to receive a syringe 30 of conventional fabrication for providing, in conjunction with pump chamber housing 18, a variable volume chamber.

As shown in FIG. 2, inlet port 20 communicates with a twin valve member 32, which comprises an umbrella portion 34 serving as a first, one-way inlet valve for inlet port 20. Double valve 32 also defines a duckbill portion 36, which serves as a second, one-way outlet valve member for outlet 22. Valve 32 may be generally constructed in accordance with U.S. Pat. No. 3,159,176. If desired, an increased outlet-bias pressure can be provided by thickening the lips 38 of duckbill section 36, so that a greater pressure is required to push them apart.

Preferably, outlet valve portion 36 is biased in the closed portion until an outlet pressure of at least about 3 p.s.i. is provided.

Porous member 40 is a hydrophobic, porous member capable of permitting the passage of gas while preventing the passage of aqueous liquid. For example, the previously mentioned Celgard 2400 Standard Laminate may be suitably used.

Administration set 10, including the valve housing 18 and the related parts, may be positioned for use in the manner shown in FIG. 3. Parenteral solution source 42, such as a solution bottle, is suspended from a conventional IV pole 44. Spike 14 penetrates the closure of solution bottle 42 for sterile access to parenteral solution. Needle hub 16 carries a needle which is positioned in an arm vein of a patient.

Syringe 30 is engaged with a syringe pump 46, which may, for example, be made in accordance with U.S. Pat. No. 3,901,231, or any other desired design. Pump 46 reciprocates the plunger 48 of syringe 30 back and forth at a predetermined rate and stroke distance, to pump solution through pump chamber 18 at the same desired, predetermined rate.

Upon every intake stroke of plunger 48, solution is sucked in from inlet line 20 through one-way valve 34. On every outlet or compression stroke of plunger 48, an increased liquid pressure is provided in the pump chamber 18, forcing liquid through pressure biased valve 36.

However, in the event that parenteral solution source 42 is exhausted, and air enters pump chamber 18 in substantial quantities, on the compression or outlet stroke of plunger 48, air will pass through porous membrane 40 back into inlet line 20, rather than being forced through biased valve 36, since that is the lower resistance path of flow or air, although it is not such for liquids. As a result, although plunger 48 continues to reciprocate in syringe 30, fluid flow through set 10 into the patient will cease, and the patient will be spared the pumped infusion or air.

Referring to FIG. 4, a different embodiment of pump chamber and related parts is shown. In this embodiment, tubing 24a, corresponding to tubing 24, communicates with an inlet chamber 50. First, upstream, one-way valve 52 is shown to be a duckbill type valve, positioned to prevent the backflow of fluid which is passed through it from inlet chamber 50.

One-way inlet valve 52 leads into pump chamber 54, which defines a port 56 adapted for communication with a syringe 60, which may be of a construction similar to syringe 30.

Biased, one-way outlet valve 58 is shown in this embodiment to be a spring-biased poppet valve. Spring 60 of valve 58 can bear against an end of tubing 26a, which may be similar to tubing 26.

Apart from that shown, the administration set which is shown in part in FIG. 4 can be identical to the administration set of FIG. 1, although other designs may also be used.

Porous, hydrophobic membrane 62 is shown in this embodiment to be supported on both sides by perforated grates 64, which are attached within housing halves 66, 68 to support porous, hydrophobic membrane 62. Membrane 62 may be similar to membrane 40.

Housing halves 66, 68 can be heat or solvent sealed together to hold the grates, membrane, and inlet valve 52 in position.

Preferably, the upper wall 66 of inlet chamber 50 is spaced only about 0.06 inch from its nearest grate 64, to prevent trapping of bubbles during priming.

The structure of FIG. 4 functions in a manner similar to that of the previous embodiment, in that, if substantial gas passes through valve 52 into chamber 54, it will be expelled back into inlet chamber 50 through membrane 62 upon pumping by syringe 60, without overcoming the resistance of outlet valve 58. Accordingly, substantial amounts of gas will not be pumped into tubing 26a, while gas-free liquid will readily pass into tubing 26a upon reciprocation of the plunger of syringe 60.

The above has been offered for illustrative purposes only, and is not for the purpose of limiting the invention of this application, which is as defined in the claims below.

That which is claimed is:

1. A multiple valve pump device which comprises a pumping chamber adapted for pressurizing and depressurizing fluid in said chamber, a first, one-way inlet valve communicating with said pumping chamber and adapted to permit fluid flow therein, a second, one-way outlet valve communicating with the pumping chamber and adapted to permit fluid flow out of said chamber, and an upstream inlet flow path for providing fluid to the pumping chamber through the inlet valve, said second outlet valve being biased to prevent outflow of fluid below a predetermined pressure, the improvement comprising, in combination, a porous member in communication with the interior of said pumping chamber on one side of said member and in communication with said inlet flow path on its other side, to permit selective fluid communication between said pumping chamber and inlet flow path through said porous member without passing through said first valve, said porous member being capable of allowing passage of a first fluid material, while preventing the passage of a second fluid material, whereby said second fluid can be pumped, but said pump device is prevented from pumping in the presence of substantial quantities of said first material.

2. The pump device of claim 1 in which said first material is a gas, the second material is aqueous liquid, and said porous member is a porous, hydrophobic membrane.

3. The pump device of claim 2, in combination with and as part of a parenteral solution administration set.

4. The pump device of claim 3 in which said pumping chamber includes port means for air-tight fluid communication with a syringe member, for providing fluid pressurization and depressurization.

5. The pump device of claim 4 in which said first and second one-way valves are defined by a single flexible member, said member defining umbrella valve means at one end thereof for defining said one-way inlet valve, and duckbill valve means at another end thereof for defining said one-way outlet valve.

6. The pump apparatus of claim 4 in which said second outlet valve is a spring-biased poppet valve.

7. The pump apparatus of claim 6 in which said porous membrane is supported between a pair of grate members which, in turn, are attached to the walls of said pumping chamber.

8. The pump apparatus of claim 4 in which a syringe member is connected to said port means for providing fluid pressurization and depressurization in said chamber.

9. The pump device of claim 1 in which said first material is aqueous liquid and said second material is a gas, said porous member being a porous, hydrophilic membrane.

* * * * *